United States Patent
Kiel

(12) 
(10) Patent No.: US 6,429,335 B1
(45) Date of Patent: Aug. 6, 2002

(54) REDUCTIVE AMINATION OF ALDEHYDES

(75) Inventor: Wolfgang Kiel, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/019,196

(22) PCT Filed: Jun. 13, 2000

(86) PCT No.: PCT/EP00/05390

§ 371 (c)(1),
(2), (4) Date: Dec. 19, 2001

(87) PCT Pub. No.: WO01/00564

PCT Pub. Date: Jan. 4, 2001

(30) Foreign Application Priority Data

Jun. 26, 1999 (DE) .......................................... 199 29 345

(51) Int. Cl.$^7$ ............................................. C07C 209/00
(52) U.S. Cl. ..................... 564/397; 564/398; 564/384; 564/389; 564/391
(58) Field of Search ................................. 564/384, 389, 564/391, 397, 398

(56) References Cited

U.S. PATENT DOCUMENTS

| 2,016,962 A | 10/1935 | Flint et al. .................. 260/127 |
| 3,187,047 A | 6/1965 | Green ...................... 260/570.8 |

FOREIGN PATENT DOCUMENTS

| EP | 0 536 939 | 4/1993 |
| EP | 0 355 351 | 2/2000 |

OTHER PUBLICATIONS

Rama Rao et al.: "Studies directed towards the total synthesis of vancomycin", Tetrahedron Letters., vol. 35, No. 45, 1995, pp. 8465–8468, XP000938770.

Peng Zhou et al.: Assignment of relative and absolute confriguration of acyclic polyols and Aminopolyols, Tetrahedron, vol. 29, No. 41, 1993, pp. 9343–9352, XP000938772.

*Primary Examiner*—Samuel Barts
(74) *Attorney, Agent, or Firm*—Joseph C. Gil; Richard E. L. Henderson

(57) ABSTRACT

The present invention relates to a process for preparing amines of formula (I)

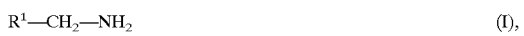

$$R^1\text{—CH}_2\text{—NH}_2 \qquad (I),$$

wherein $R^1$ represents optionally branched $C_1$–$C_{12}$-alkyl, $C_3$–$C_8$-cycloalkyl, $C_6$–$C_{12}$-aryl or $C_6$–$C_{12}$-aryl substituted with halogen-and/or $C_1$–$C_{12}$-alkyl, $C_7$–$C_{10}$-aralkyl or $C_7$–$C_{10}$-aralkyl substituted on the aryl radical by halogen and/or $C_1$–$C_{12}$-alkyl, or an aldose residue of the formula $C_iH_{2i+1}O_i$ in which i is 2 to 5 and wherein one hydrogen of the aldose residue is optionally replaced by a saccharide residue, by catalytically hydrogenating aldehydes of formula (II)

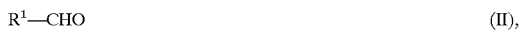

$$R^1\text{—CHO} \qquad (II),$$

wherein $R^1$ has the meaning indicated for formula (I), in the presence of ammonia, a hydrogenation catalyst, and disodium tetraborate.

11 Claims, No Drawings

REDUCTIVE AMINATION OF ALDEHYDES

The present invention relates to a process for preparing aliphatic and aromatic amines by catalytic hydrogenation of the corresponding aldehydes in the presence of ammonia, disodium tetraborate, in particular the decahydrate (borax), and a catalyst.

The preparation of aliphatic amines by reacting aliphatic aldehydes or ketones with ammonia and hydrogen in the presence of a hydrogenation catalyst is known. The advantageous addition of organic acids, for example acetic acid, or their ammonium salts is also described (for example EP-A-355 351, EP-A-536 939, U.S. Pat. No. 3,187,047). This considerably increases the selectivity of the reaction, in particular by repressing competing alcohol formation.

EP-A-355 351 describes a process for preparing amines containing at least one aromatic radical having one to three halogen substituents. In this case it is possible to minimize unwanted dehalogenations by suitable additions. The maximum yield of amines starting from an oxo compound is 91.8%.

U.S. Pat. No. 3,187,047 discloses the reductive amination of ketones with addition of an ammonium salt of an organic acid. Nothing is said about the use of aldehydes.

EP-A-536 939 discloses a process for preparing amino polyols by reductive amination of a saccharide. Addition of a compound which liberates ammonium ions under the reaction conditions, in particular of an organic acid or its ammonium salt, markedly increases the yield of amino polyol. Nevertheless, the maximum yield of amino polyol obtained is 88.6%.

Aliphatic and aromatic amines have a large number of possible applications in the areas of crop protection and pharmacology. Use in these sectors and economic reasons make a high degree of purity necessary. In order nevertheless to keep the expenditure on purification low, the preparation processes must meet high demands in relation to selectivity and thus the purity of the crude product.

The object of the present invention was to develop a process for preparing aromatic and aliphatic amines which ensures a high degree of selectivity with good conversions.

It has now been found that the addition of disodium tetraborate in place of an organic acid or its ammonium salt is advantageous in the amination of aldehydes.

Disodium tetraborate for the purpose of the process of the invention comprises anhydrous disodium tetraborate and its various hydrates, in particular disodium tetraborate decahydrate (borax).

The invention accordingly relates to a process for preparing amines of the formula (I)

$$R^1\text{---}CH_2\text{---}NH_2 \qquad (I),$$

where $R^1$ represents optionally branched $C_1$–$C_{12}$-alkyl, $C_3$–$C_8$-cycloalkyl, optionally halogen- and/or $C_1$–$C_{12}$-alkyl-substituted $C_6$–$C_{12}$-aryl, $C_7$–$C_{10}$-aralkyl which is optionally substituted on the aryl radical by halogen and/or $C_1$–$C_{12}$-alkyl, or an aldose residue of the formula $C_iH_{2i+1}O_i$ with i=2–5 or an aldose residue of the preceding formula where one hydrogen is replaced by a saccharide residue, by catalytic hydrogenation of aldehydes of the formula (II)

$$R^1\text{---}CHO \qquad (II),$$

where $R^1$ has the meaning indicated for formula 1, in the presence of ammonia and of a hydrogenation catalyst, characterized in that the reaction is carried out in the presence of disodium tetraborate.

Borax, disodium tetraborate decahydrate, is particularly suitable as disodium tetraborate.

Compared with the use of acetic acid, the yields of desired product are increased by more than 10% by use of disodium tetraborate.

A reaction procedure with addition of disodium tetraborate is also distinguished from known processes in that on use of nickel or cobalt catalysts as hydrogenation catalysts they undergo considerably less attack with formation of nickel or cobalt ions than was previously the case. This leads to a markedly increased useful life of the hydrogenation catalyst with unchanged selectivity and activity. In fact, the hydrogenation catalyst gains selectivity after the first use. This favors a continuous reaction procedure or makes it possible for the first time.

Starting materials used in the process of the invention are aldehydes of the formula (II). $R^1$ therein preferably represents optionally halogen- and/or $C_1$–$C_4$-alkyl-substituted $C_6$–$C_{12}$-aryl, $C_7$–$C_{10}$-aralkyl which is optionally substituted on the aryl radical by halogen and/or $C_1$–$C_4$-alkyl, or an aldose residue of the formula $C_iH_{2i+1}O_i$ with i=2–5. Examples which may be mentioned are: glucose, maltose, lactose, dihydroxypropionaldehyde, butyraldehyde, glutaraldehyde, benzaldehyde, 2-chlorobenzaldehyde, 2,4-dichlorobenzaldehyde, 4-fluorobenzaldehyde and propionaldehyde.

Aliphatic and aromatic amines of the formula (I) can be obtained by the process of the invention. $R^1$ in this case preferably represents optionally halogen- and/or $C_1$–$C_4$-alkyl-substituted $C_6$–$C_{12}$-aryl, $C_7$–$C_{10}$-aralkyl which is optionally substituted on the aryl radical by halogen and/or $C_1$–$C_4$-alkyl, or an aldose residue of the formula $C_iH_{2i+1}O_i$ with i=2–5. Examples of amines obtainable according to the invention which may be mentioned are: aminosorbitol, 1-aminopropanediol, 1-aminobutane, glutaramine(1), benzylamine, 2-chlorobenzylamine, 2,4-dichlorobenzylamine and 4-fluorobenzylamine.

The process of the invention is carried out in the presence of a hydrogenation catalyst. Such hydrogenation catalysts are sufficiently well known to the skilled worker. A nickel or cobalt catalyst is used in a preferred embodiment. It is possible to employ, for example, Raney nickel or Raney cobalt. Further suitable hydrogenation catalysts are, for example, nickel or cobalt in metallic or oxidic form, optionally applied to a support. Suitable supports are, inter alia, silica or aluminas, for example $Al_2O_3$ in the various modifications.

The amount of catalyst in the reaction mixture can be between 2 and 15% by weight, based on the aldehyde employed. The catalyst can be reused several times so that the resulting amount of catalyst required is less than 0.3% by weight based on the total amount of converted aldehyde.

The hydrogenation can be carried out, for example, in the liquid phase or on a fixed bed catalyst.

The process of the invention is carried out at temperatures from 60° C. to 250° C. Temperatures of from 90° C. to 120° C. are advantageously used.

The hydrogen pressure can vary from 20 bar to 250 bar. A hydrogen pressure of from 80 bar to 140 bar is preferred.

A batchwise or continuous procedure is possible. Suitable for the batchwise reaction procedure is, for example, an autoclave or a stirred reactor, and for the continuous reaction procedure is, for example, a tubular reactor.

Ammonia is added in excess relative to the aldehyde employed in the process of the invention. The molar ratio of ammonia employed to the amount of aldehyde to be converted may be between 20:1 and 2:1. A ratio of ammonia to aldehyde between 10:1 and 5:1 is preferred.

The process of the invention can be carried out with or without solvent. The use of a solvent is preferred. The proportion of the solvent in the reaction mixture can be, for example, 10% by weight to 90% by weight, this proportion preferably being 40% by weight to 60% by weight.

Suitable solvents are water, alcohols and hydrocarbons, each of which can be used singly or as mixtures. Preferred solvents are water and alcohols. Examples of suitable alcohols which may be mentioned are methanol, ethanol and isopropanol, and examples of suitable hydrocarbons which may be mentioned are toluene, cyclohexane and methylcyclohexane.

In a preferred embodiment, the process of the invention is carried out in the presence of a solvent or mixture of solvents selected from the group of water, methanol and ethanol.

Disodium tetraborate or a hydrate thereof, in particular disodium tetraborate decahydrate, is added according to the invention to the reaction mixture. Disodium tetraborate may be added in an amount of from 0.5% by weight to 10% by weight, preferably in an amount of from 3% by weight to 7% by weight, based on the aldehyde to be converted.

If aldehydes substituted by halogen or a halogen-containing radical are employed in the process of the invention, it is advantageous to add a sulfur compound to the reaction mixture. The sulfur compound can be added to the hydrogenation catalyst directly or mixed with an aldehyde to be converted. Examples of suitable sulfur compounds which may be mentioned are dimethyl sulfoxide and bis(2-hydroxyethyl) sulfide. Based on catalyst employed, where appropriate 3% by weight to 20% by weight, preferably 5% by weight to 10% by weight, of sulfur compound are added.

The process of the invention has proved particularly suitable for the reductive amination of 2-chlorobenzaldehyde and glucose to form 2-chlorobenzylamine and 1-aminosorbitol respectively.

The process of the invention for preparing amines from aldehydes is explained further by means of the following examples without intending it to be restricted to these examples in any way.

EXAMPLES

Example 1 o-Chlorobenzylamine

The following are introduced into a 0.7 l autoclave:

100 g of methanol 4 g of Ra Ni 0.2 g of bis(2-hydroxyethyl) sulfide 2.9 g of borax 80 g of ammonia After the autoclave has been rendered inert with nitrogen, the autoclave is heated to 100° C. and charged with 140 bar of hydrogen.

Over the course of 60 min, 141 g of o-chlorobenzylaldeyde are pumped in under these conditions. After cooling to 50° C., decompression to 1 bar and removal of the catalyst by filtration, a crude product of the following composition is obtained:

| o-chlorobenzylamine: | 95.87% |
| o-chlorobenzyl alcohol: | 3.19% |
| benzylamine: | 0.1% |
| unknown components: | 0.84% |

The percentage data are area percent resulting from the analysis of the crude product by gas chromatography. Purification of the crude product is possible by distillation.

Example 2

1-Aminosorbitol (on First Use of the Catalyst)

The following are introduced into a 0.7 l autoclave:

50 g of water 8 g of Ra Co 2.9 g of borax

After the autoclave has been rendered inert with nitrogen, the autoclave is heated to –90° C. and charged with 140 bar of hydrogen.

Over the course of 60 min, 120 g of glucose monohydrate dissolved in 70 g of water are pumped in under these conditions.

After cooling to 50° C., decompression to 1 bar and removal of the catalyst by filtration, a crude product with a 1-aminosorbitol yield of 74% of theory (GC area percent) is obtained.

Example 3

1-Aminosorbitol (on Second Use of the Catalyst)

Procedure as for example 2 but the catalyst used in example 2 is employed anew as catalyst.

Yield: 94.9% of theory (GC area percent).

Example 4

1-Aminosorbitol (on Subsequent Uses of the Catalyst)

The catalyst was then employed several times repeatedly (up to 20 times): The yields were in each case between 92–95% of theory (GC area percent).

Example 5 (Comparative Example 1)

1-Aminosorbitol (Use of Glacial Acetic Acid in Place of Borax)

Procedure as in example 2 but 1.5 g of glacial acetic acid were used as additional reagent in place of borax.

Yield: 62.0% of theory (GC area percent)

Example 6 (Comparative Example 2)

1-Aminosorbitol (Use of Glacial Acetic Acid in Place of Borax)

Procedure as in example 5. However, the catalyst used previously was employed anew.

The yield was then: 81.0% of theory (GC area percent)

Comparison of examples 2–4 with examples 5–6 shows that the use of borax increases the yields of desired amine by about 10%.

What is claimed is:

1. A process for preparing an amine of the formula (I)

$$R^1-CH_2-NH_2 \quad (I),$$

wherein $R^1$ represents optionally branched $C_1$–$C_{12}$-alkyl, $C_3$–$C_8$-cycloalkyl, $C_6$–$C_{12}$-aryl or $C_6$–$C_{12}$-aryl substituted with halogen-and/or $C_1$–$C_{12}$-alkyl, $C_7$–$C_{10}$-aralkyl or $C_7$–$C_{10}$-aralkyl substituted on the aryl radical by halogen and/or $C_1$–$C_{12}$-alkyl, or an aldose residue of the formula $C_iH_{2i+1}O_i$ in which i is 2 to 5 and wherein one hydrogen of the aldose residue is optionally replaced by a saccharide residue,
comprising catalytically hydrogenating an aldehyde of the formula (II)

$$R^1-CHO \quad (II),$$

wherein $R^1$ has the meaning indicated for formula (I), in the presence of ammonia, a hydrogenation catalyst, and disodium tetraborate.

2. The process according to claim 1 wherein disodium tetraborate is used as the decahydrate.

3. The process according to claim 1 wherein the hydrogenation catalyst is a nickel or cobalt catalyst.

4. The process according to claim 3 wherein the hydrogenation catalyst is selected from the group consisting of Raney nickel, Raney cobalt, supported nickel, supported cobalt, supported nickel oxide, and supported cobalt oxide.

5. The process according to claim 1 wherein the amount of the catalyst, calculated as metal, is from 2 to 15% by weight, based on the aldehyde.

6. The process according to claim 1 wherein a sulfur compound is additionally present.

7. The process according to claim 6 wherein the sulfur compound is selected from the group consisting of dimethyl sulfoxide and bis(2-hydroxyethyl) sulfide.

8. The process according to claim 1 wherein 10 to 90% by weight of one or more solvents selected from the group consisting of water, alcohol, and one or more hydrocarbons is additionally present.

9. The process according to claim 8 wherein a sulfur compound is additionally present.

10. The process according to claim 1 wherein the disodium tetraborate is added as disodium tetraborate decahydrate in an amount of 0.5 to 10% by weight, based on the aldehyde.

11. The process according to claim 1 wherein the molar ratio of ammonia to aldehyde is between 20:1 and 2:1.

* * * * *